US009416654B2

United States Patent
Lee et al.

(10) Patent No.: US 9,416,654 B2
(45) Date of Patent: Aug. 16, 2016

(54) COMPOUND SAMPLE EXTRACTION APPARATUS

(75) Inventors: Gun-Chang Lee, Gyeonggi-do (KR); Dong-Jin Ham, Gyeonggi-do (KR); Sang-Bum Chi, Seoul (KR); Kyeong-Hong Kim, Gyonggi-do (KR)

(73) Assignee: KOREA INSTITUTE OF OCEAN SCIENCE & TECHNOLOGY, Ansan-Si, Gyeonggi-Do (KR)

( * ) Notice: Subject to any disclaimer, the term of this patent is extended or adjusted under 35 U.S.C. 154(b) by 274 days.

(21) Appl. No.: 14/233,695

(22) PCT Filed: Aug. 3, 2012

(86) PCT No.: PCT/KR2012/006196
§ 371 (c)(1),
(2), (4) Date: Jan. 17, 2014

(87) PCT Pub. No.: WO2013/022233
PCT Pub. Date: Feb. 14, 2013

(65) Prior Publication Data
US 2014/0144255 A1    May 29, 2014

(30) Foreign Application Priority Data
Aug. 11, 2011    (KR) .......................... 10-2011-0080250

(51) Int. Cl.
*E21B 49/02*     (2006.01)
*G01N 1/04*      (2006.01)
*G01N 1/10*      (2006.01)

(52) U.S. Cl.
CPC .............. *E21B 49/025* (2013.01); *E21B 49/02* (2013.01); *G01N 1/04* (2013.01); *G01N 2001/1093* (2013.01)

(58) Field of Classification Search
CPC ..... E21B 49/001; E21B 49/02; E21B 49/025; E21B 49/08; G01N 2001/1093
USPC ....................................................... 73/864.65
See application file for complete search history.

(56) References Cited

U.S. PATENT DOCUMENTS 3,996,678 A * 12/1976 Amann ................. E21B 49/025
                                                          212/84
4,116,069 A *  9/1978 Lezgintsev .............. E21B 25/18
                                                          37/186

(Continued)

FOREIGN PATENT DOCUMENTS

KR    10-0727590    6/2007
KR    10-0732395    6/2007

(Continued)

OTHER PUBLICATIONS

International Search Report of corresponding PCT/KR2012/006196, dated Feb. 15, 2013, 6 pages.

(Continued)

*Primary Examiner* — Freddie Kirkland, III
(74) *Attorney, Agent, or Firm* — Lewis Roca Rothgerber Christie LLP (57) ABSTRACT

Disclosed is a complex sampling apparatus. The complex sampling apparatus includes a main sampling unit having a predetermined weight to be sunk to sea floor and inserted into the sea floor in order to collect a sample including a sediment; one or a plurality of sub-sampling unit disposed at a side of the main sampling unit to detect that the sub-sampling unit arrives on the sea floor and to scrape a predetermined amount of the sample from a surface of the sea floor; and an image acquiring unit installed to the main sampling unit to acquire an image of the sea floor.

8 Claims, 8 Drawing Sheets

(56) References Cited

U.S. PATENT DOCUMENTS

| | | | | |
|---|---|---|---|---|
| 4,184,758 | A | * | 1/1980 | Winnacker ............ G03B 17/08 396/25 |
| 4,709,584 | A | * | 12/1987 | Voll ....................... E21B 25/18 73/864.44 |
| 5,385,827 | A | | 1/1995 | Clark |
| 6,283,675 | B1 | * | 9/2001 | Dulsey ..................... B09C 1/08 405/128.5 |
| 8,109,223 | B2 | * | 2/2012 | Jamieson ............... B63G 8/001 114/312 |
| 8,191,436 | B2 | * | 6/2012 | Chun ................... E21B 49/025 73/864.44 |
| 8,908,476 | B2 | * | 12/2014 | Chun ..................... B63G 8/001 114/312 |
| 2012/0204781 | A1 | * | 8/2012 | Chun ..................... B63G 8/001 114/312 |

FOREIGN PATENT DOCUMENTS

| KR | 10-1046577 | 6/2010 |
|---|---|---|
| KR | 10-2011-0088461 | 8/2011 |

OTHER PUBLICATIONS

Lee, et al., "Examination of Correction Factor for Manganese Nodule Abundance using the Free Fall Grab and Box Corer," The Sea—Journal of the Korean Society of Oceanography, vol. 13, No. 3, pp. 280-285, Aug. 2008.

\* cited by examiner

COMPOUND SAMPLE EXTRACTION APPARATUS

CROSS-REFERENCE TO RELATED APPLICATIONS

This application is a National Phase Patent Application and claims priority to and benefit of International Application Number PCT/KR2012/006196, filed on Aug. 3, 2012, which claims priority to and benefit of Korean Patent Application Number 10-2011-0080250, filed on Aug. 11, 2011 the entire disclosures of which are incorporated herein by reference.

TECHNICAL FIELD

The present invention relates to a sampling apparatus, and more particularly, to a complex sampling apparatus capable of simultaneously collecting a sample from the same area of the sea floor in a free-fall type and a box type.

BACKGROUND ART

In general, a specific type of sampler has been widely used to explore for a manganese nodule.

Since the manganese nodules are distributed over a wide area of a deep sea floor, a free-fall grab (FFG) is used to reduce the time taken to collect a sample, and to accurately conduct a statistical analysis and a sample analysis.

Since the FFG is dropped into sea without any wires connected to a research ship, several FFGs may be simultaneously used at one fixed point. The FFG has a sampling time shorter than that of a box corer (BC).

However, the FFG can only recover the manganese nodules scattered in a surface layer, but cannot collect the manganese nodules mixed with sediment.

Even when collecting manganese nodules on a surface layer, due to an error of a machine operated to recover the manganese nodules through the FFG, manganese nodules having large sizes may be gained. In addition, if a manganese nodule lodges at an edge of a sample collecting net of the FFG, since the net is not fully closed, a small size of a manganese nodule may be lost while the FFG is being recovered to the surface of a sea.

One example of the related art is disclosed in Korean Patent No. 10-1046577 (issued on Jun. 29, 2011). A collecting apparatus disclosed in Korean Patent No. 10-1046577 is capable of sampling each layer of bottom seawater near seabed.

Recently, the BC has been used to reduce the sampling time. Without any disturbance, sediment is collected together with manganese nodules distributed on seabed, so that the manganese nodules in the sediment may be obtained.

Thus, the abundance may be estimated, which is more approximate to the actual abundance than that by the method using the FFG.

However, when samples are collected at the same point by using both devices, it is impossible to collect samples exactly at the same point due to a factor such as an ocean current or a current meteorological state.

Further, the sampling time may be significantly increased.

In addition, the samples collected by both devices cannot be compared with each other and the collecting efficiency of the FFG cannot be measured.

DISCLOSURE

Technical Problem

An object of the present invention is to provide a complex sampling apparatus capable of simultaneously collecting samples such as a manganese nodule from the same area of sea floor by using both FFG (Free-Fall Grab) and BC (Box Corer).

Another object of the present invention is to provide a complex sampling apparatus capable of using both FFG and BC simultaneously or independently from each other in order to collect samples from sea floor.

Still another object of the present invention is to provide a complex sampling apparatus capable of supplementing disadvantages of the FFG and BC with each other in the aspect of the sampling result from sea floor.

Technical Solution

The present invention provides a complex sampling apparatus.

The complex sampling apparatus includes a main sampling unit having a predetermined weight to be sunk to sea floor and inserted into the sea floor in order to collect a sample including a sediment; one or a plurality of sub-sampling unit disposed at a side of the main sampling unit to detect that the sub-sampling unit arrives on the sea floor and to scrape a predetermined amount of the sample from a surface of the sea floor; and an image acquiring unit installed to the main sampling unit to acquire an image of the sea floor.

Preferably, the main sampling unit includes a weight connected to a wire wound by an external force; a sample box installed to a bottom end of the weight and having an opened bottom end to temporarily store the sample and the sediment; a spreader hinged to the weight and having one end connected to the wire and an opposite end tightly sealing an opening of the sample box; and a support frame to support the weight, the support frame having a lower end landed on the sea floor The sub-sampling units are disposed to both sides of the main sampling unit.

Preferably, the sub-sampling unit includes an extension frame extending to a side of the support frame; a pair of grabs formed in a plate shape, and having one ends hinged to the extension frame, in which ends of the grabs are connected to each other through a mesh net; an elastic member to provide an elastic force in a direction allowing the pair of grabs to be closed to each other; a fixing member hinged to the extension frame to fix the grabs to allow the grabs to be away from each other; and a trigger stood up to be elevated on the extension frame and to release a fixed state of the fixing member by using the wire when a bottom end of the trigger is touched to the sea floor to receive an external force.

The fixing member may include a fixing protrusion inserted into a fixing groove formed on a circumference of one of the grabs.

The trigger may include a roller rotated on a top end of the trigger.

The roller may be connected to the fixing protrusion through a wire.

The sub-sampling unit includes a supplementary weight storage unit which may be detachably coupled to the sub-sampling unit and stores a predetermined amount of a heavy material.

The supplementary weight storage unit may include a rotational door to open or close the supplementary weight storage unit in cooperation with the elevation operation of the trigger.

Preferably, the extension frame is detachably coupled to the support frame.

The extension frame may include a multi-stage pipe, a length of which is adjustable in a side direction.

Preferably, the weight includes a plurality of unit weights different from each other, and its weight is adjusted by adjusting a number of the unit weights.

Advantageous Effects

As described above, the present invention may collect samples such as a manganese nodule from the same area of sea floor by simultaneously using both FFG and BC.

Further, the present invention may use both FFG and BC simultaneously or independently from each other in order to collect samples from sea floor.

In addition, the present invention may supplement disadvantages of the FFG and BC with each other in the aspect of the sampling result from sea floor.

BEST MODE

Mode for Invention

Hereinafter, a plant for producing microalgae biofuel according to the present invention will be described with reference to accompanying drawings.

Hereinafter, a complex sampling apparatus according to an embodiment of the present invention will be described with reference to accompanying drawings.

Figure 1:
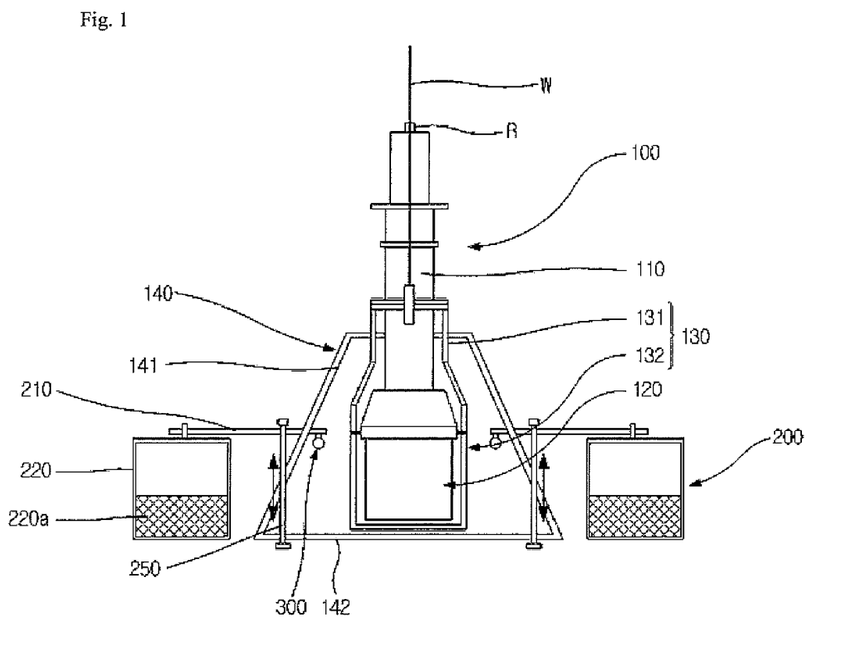
FIG. 1 is a schematic view showing a complex sampling apparatus according to an embodiment of the present invention.

FIG. 1 is a schematic view showing a complex sampling apparatus according to an embodiment of the present invention.

Main Sampling Unit 100

Referring to FIG. 1, the complex sampling apparatus includes a main sampling unit 100, a sub-sampling unit 200 and an image acquiring unit 300.

The main sampling unit 100 may be a box corer.

The main sampling unit 100 includes a weight 110, a sample box 120, a spreader 130 and a support frame 140.

The weight 110 has a predetermined length in a longitudinal direction and a predetermined weight or more.

A top end of the weight 110 is connected a wire W having a predetermined length. The wire W is connected to a winding device in a base ship located on a sea surface.

The sample box 120 is installed on a bottom end of the weight 110.

The sample box 120 has a space for containing a predetermined amount of samples therein and an opened bottom end.

Preferably, an edge of the bottom end of the sample box 120 may be formed to be tapered along the bottom end, that is, to be sharp.

The spreader 130 includes a rotation bar 131 and a cover member 132 mounted on an end of the rotation bar 131 and having an area to tightly seal up an opening of the sample box 120.

The rotation bar 131 is hinged to the weight 110.

The cover member 132 is installed on one end of the rotation bar 131.

The opposite end of the rotation bar 131 may be connected to the wire W connected to the top end of the weight 110.

In this case, a roller R is mounted on the top end of the weight 110 and the wire W is guided through the roller R to be connected to the opposite end of the rotation bar 131.

Thus, the rotation bar 131 is rotated in a predetermined direction according to an operation of pulling the wire W, and the cover member 120 shuts or opens the opening of the sample box 120 according to the rotation of the rotation bar 131.

The support frame 140 supports the weight 110 and a bottom end of the support frame 140 is safely landed on the surface of a sea floor.

The support frame 140 may include a first support frame 141 for supporting the weight 110 and a second support frame 142 extending from both ends of the first support frame 141 in a lower direction to be safely landed on the surface of sea floor.

Sub-Sampling Unit 200

Figure 7:
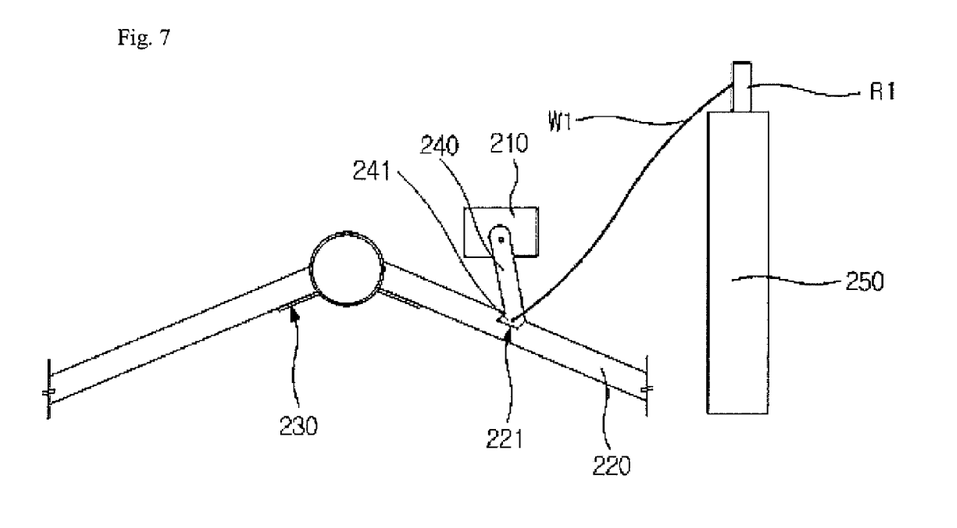
FIG. 7 is a schematic view showing a state of a grab before the grab is operated according to an embodiment of the present invention.

Referring to FIGS. 1 and 7, the sub-sampling unit 200 is installed at a side of the main sampling unit 100.

The sub-sampling units 200 may be installed at both sides of the main sampling unit 100.

Of course, the plurality of sub-sampling units 200 may be installed around the main sampling unit 100 in a space where the sub-sampling units 200 do not interfere with the rotation of the spreader 130.

The configuration of the sub-sampling unit 200 will be described below.

The sub-sampling unit 200 includes an extension frame 210, a pair of grabs 220, an elastic member 230, a fixing member 240 and a trigger 250.

The extension frame 210 extends from a side of the support frame 140 at a predetermined length.

The pair of grabs 220 together form a hinge shaft so that the grabs 200 may be close to or away from each other.

Ends of the pair of grabs 220 are connected to each other through a mesh net 220a.

One ends of the grabs 220 may constitute the hinge shaft at the extension frame 210.

The elastic member 230 is installed at the hinge shaft to allow the pair of grabs 220 to be always folded or close to each other.

The elastic member 230 may be a torsion spring.

The fixing member 240 is hinged to the extension frame 210 such that the fixing member 240 may be rotated.

A fixing protrusion 241 having a bent shape is formed on an end of the fixing member 240.

The fixing protrusion 241 is fixedly inserted into a fixing groove 221 formed at an outside of one of the grabs 220.

In this case, the fixing protrusion 241 is fixedly inserted into the fixing groove 221, then the pair of grabs 220 are forcibly separated or open from each other.

The trigger 250 is supported by the extension frame 210 and is disposed to be movable upward and downward in a standing-up state.

A roller R1 is mounted on the top end of the trigger 250.

The roller R1 is connected to the fixing protrusion 241 of the fixing member 240 through a wire W1.

In this case, when the trigger 250 moves up, the wire W1 pulls the fixing protrusion 241, so that the fixing protrusion 241 is separated from the fixing groove 221.

Thus, the pair of grabs 220 is closed due to the elastic restoring force of the elastic member 230.

Image Acquiring Unit 300

The image acquiring unit 300, which may be a camera, acquires a still picture or a moving picture of the sampling operations of the main sampling unit 100 and the sub-sampling unit 200. Then, the image acquiring unit 300 transmits the still picture or the moving picture to a storage unit installed in the base ship and connected through an electric wire or allows the still picture or the moving picture to be displayed on a display.

Hereinafter the operation of the complex sampling apparatus having the above-described configuration according to the present invention will be described.

Figure 2:
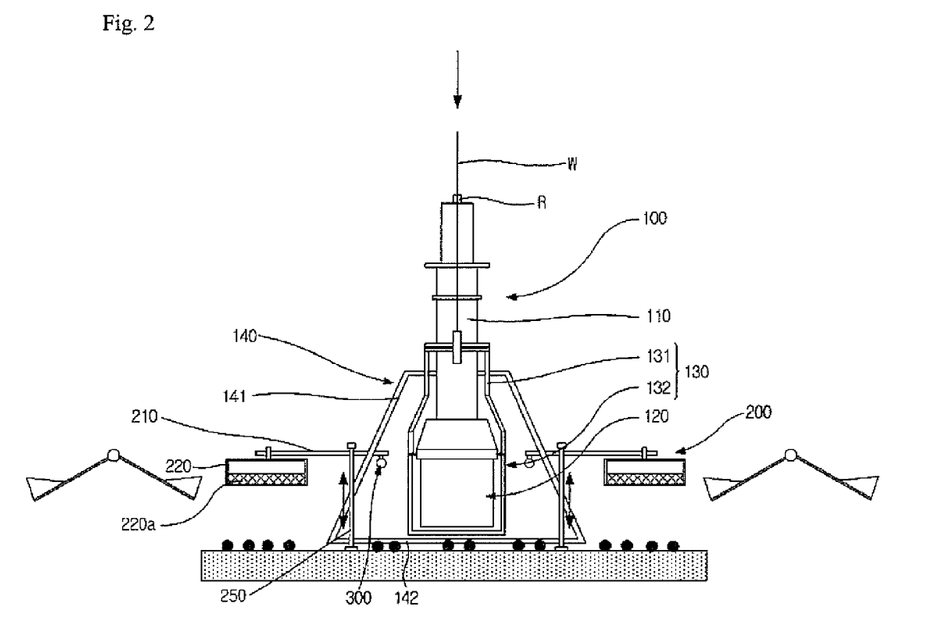
FIG. 2 is a schematic view showing a state that a complex sampling apparatus is landed on the surface of sea floor.

FIG. 2 is a schematic view showing a state of the complex sampling apparatus before the complex sampling apparatus is placed at sea floor.

Referring to FIG. 2, when the wire W is unwound by using the winding device of the base ship, the complex sampling apparatus according to the present invention may be put into sea floor.

Since the weight 110 of the main sampling unit 100 has a predetermined weight or more, the sampling apparatus may easily go down into underwater.

At this time, the main sampling unit 100 is not moved down and the grabs 220 of the sub-sampling unit 200 are kept in an open state.

Figure 3:
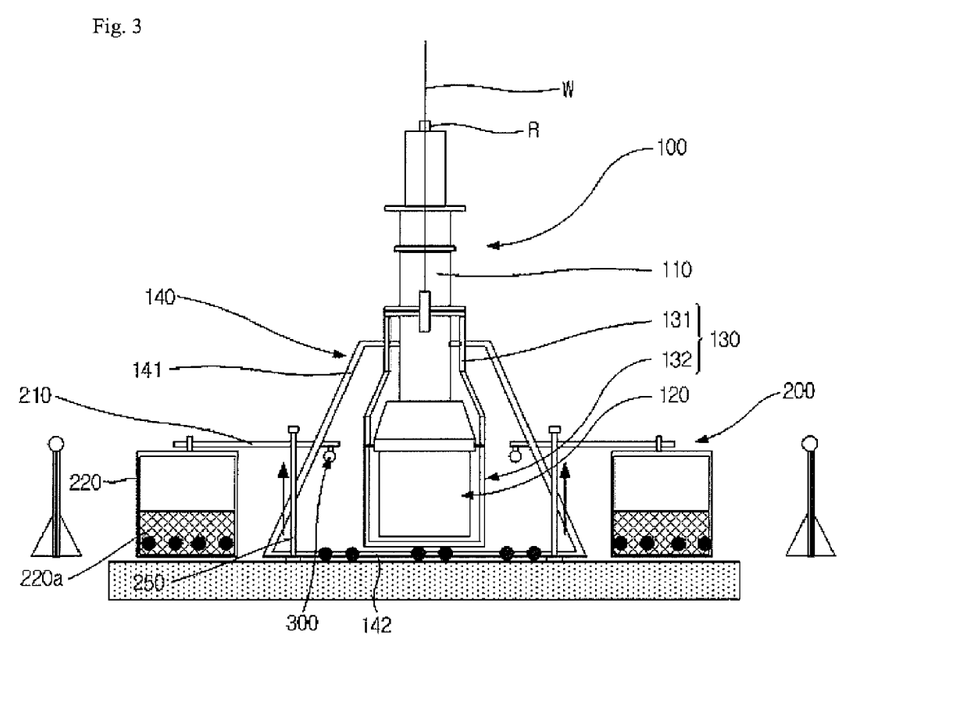
FIG. 3 is a schematic view showing an operation of a sub-sampling unit according to an embodiment of the present invention.
Figure 4:
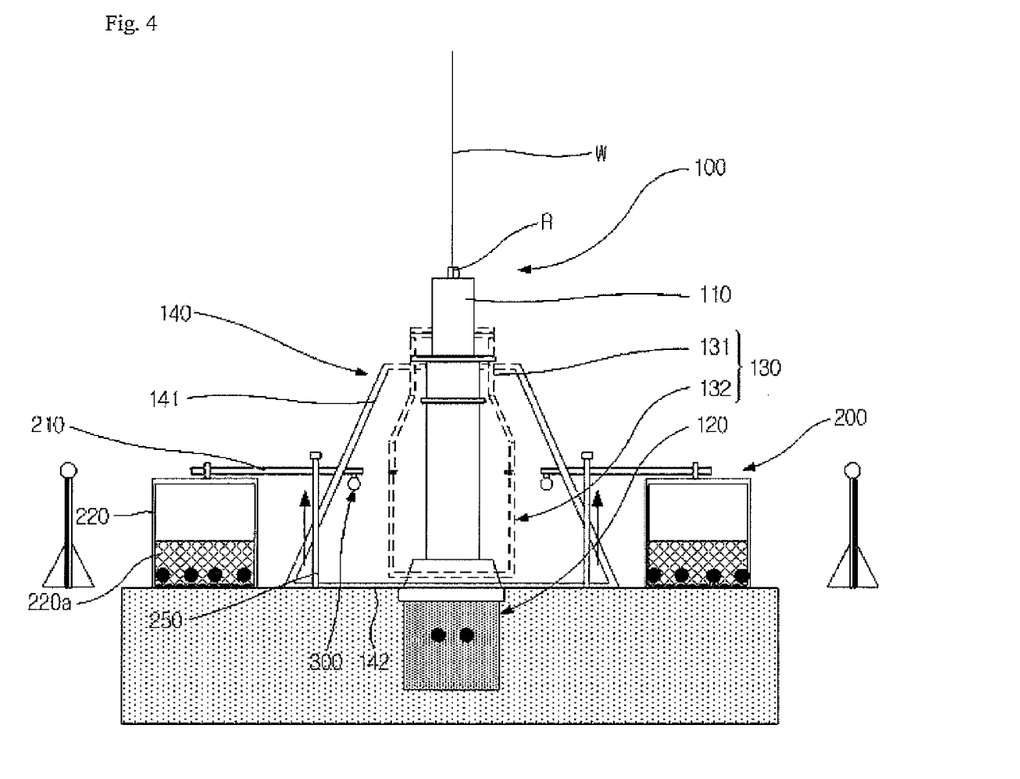
FIG. 4 is a schematic view showing an operation of a main-sampling unit according to an embodiment of the present invention.

FIGS. 3 and 4 show states that the sampling apparatus deployed to sea floor collects samples after being safely landed on a surface of sea floor.

Referring to FIG. 3, the sampling apparatus is safely landed on a surface of sea floor.

The lower end of the support frame 140 of the main sampling unit 100 is safely landed on the surface of sea floor.

In this case, while the trigger 250 of the sub-sampling unit 200 is safely landed on the surface of sea floor, the trigger 250 flows upward.

Figure 8:
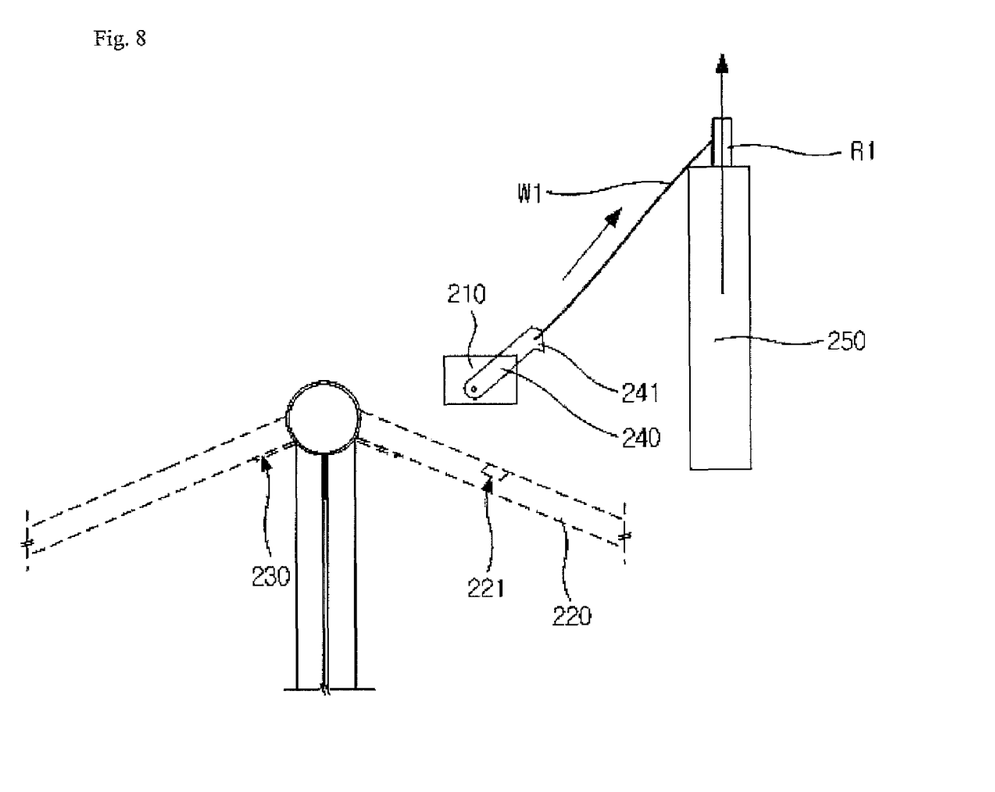
FIG. 8 is a schematic view showing a state of a grab after the grab is operated according to an embodiment of the present invention

As shown in FIGS. 7 and 8, as the trigger 250 flows upward, the wire W1 connected to the roller R1 may be pulled upward.

At the same time, the fixing protrusion 241 of the fixing member 240 connected to the opposite end of the wire W1 is rotated.

That is, the fixing protrusion 241 of the fixing member 240 may be separated from the fixing groove 221 of the grab 220.

Thus, the splayed state of the pair of grabs 220 may be released.

The pair of grabs 220 may be closed to each other by the elastic restoring force of the elastic member 230 installed at the hinge shaft.

The pair of grabs 220 closed to each other may scrape samples such as manganese nodules existing on the surface of sea floor.

The scraped samples are accumulated in the mesh net 220a connecting the pair of grabs 220 to each other.

According to the above-described operation, as soon as at least one sub-sampling unit 200 is landed on the surface of sea floor, each sub-sampling unit 220 may scrape a predetermined amount of samples existing on the surface of sea floor and may keep the samples therein.

Figure 5:
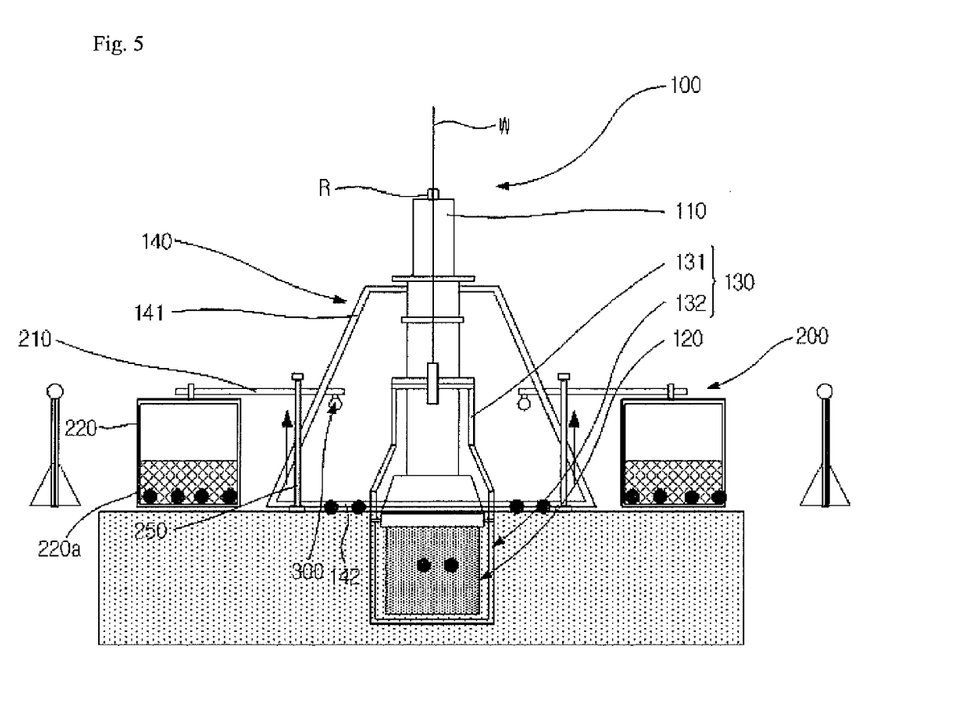
FIG. 5 is a schematic view showing another operation of a main-sampling unit according to an embodiment of the present invention.

FIG. 5 shows a sampling operation of the main sampling unit.

Meanwhile, when the main sampling unit 100 according to the present invention arrives on the surface of sea floor, the sample box 120 installed at the bottom end of the weight 110 may be inserted into sea floor by the load of the weight 110.

According to the present invention, the bottom end of the sample box 120 may be formed to be sharp so that the sample box 120 may be easily put into sea floor.

Figure 6:
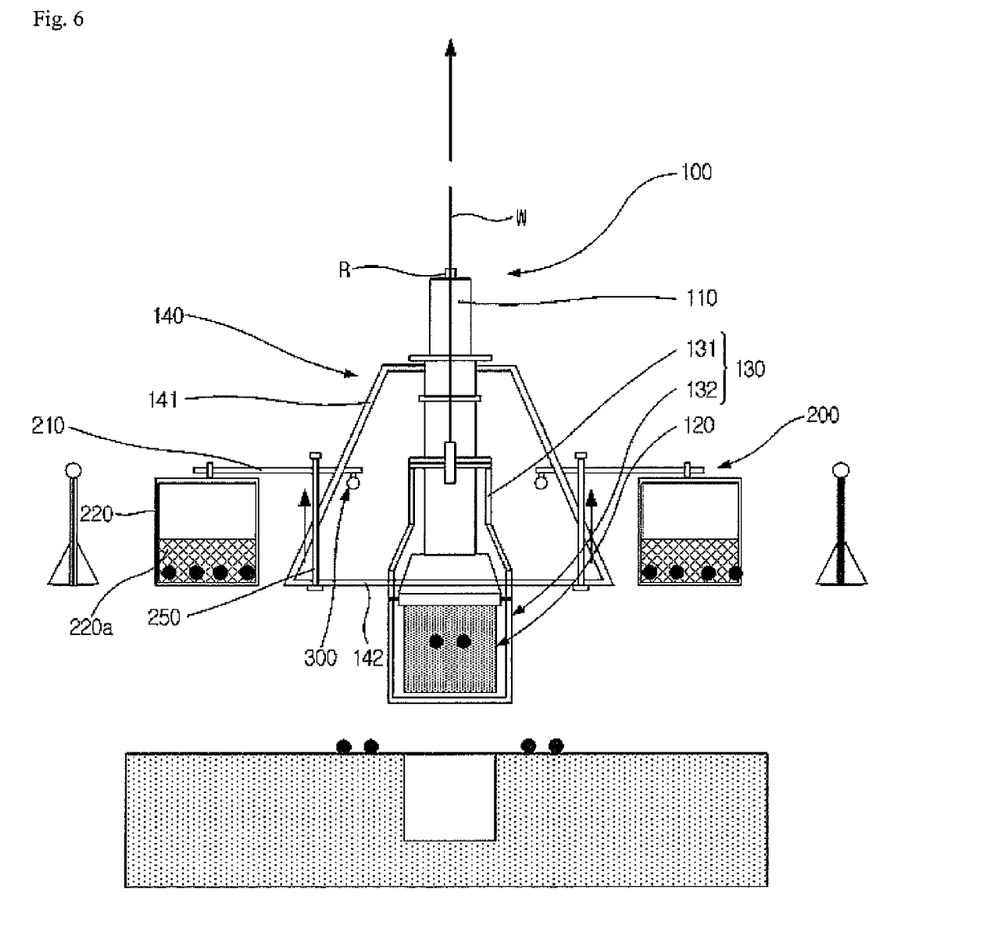
FIG. 6 is a schematic view showing still another operation of a main-sampling unit according to an embodiment of the present invention.

FIG. 6 shows a state that the samples collected by the main sampling unit moves upward.

Referring to FIG. 6, the sample box 120 is inserted into sea floor.

The wire W again moves upward by the operation of the winding device.

In this case, the rotation bar connected to the wire W through the roller R installed to the top end of the weight is rotated upward about the hinge shaft.

Thus, the cover member 132 installed to the end of the rotation bar 131 is rotated downward.

The cover member 132 rotated downward closes the bottom end opening of the sample box 120.

A sample such as a predetermined amount of manganese nodules and sediment is received in the sample box 120 and the received sample is tightly covered by the cover member 132.

According to the embodiment of the present invention, samples may be collected into a research ship, which may be a base ship, through the main sampling unit and the plurality of sub-sampling units.

According to the embodiment of the present invention, since there is no need to provide an additional weight to the sub-sampling unit which is an FFG, the sub-sampling unit may be easily constructed and may be easily attached to a side of the main sampling unit.

Meanwhile, as not shown, the weight of the main sampling unit according to the embodiment of the present invention may include unit weights.

Since the plurality of unit weights constitutes the weight thrown into sea floor, the required weight may be variably designed.

In addition, as not shown, the sub-sampling units may be detachably installed to the sides of the main sampling unit.

That is, the extension frame of the sub-sampling unit may be detachably coupled to the support frame of the main sampling unit through a coupling unit such as a bolt and a nut.

Thus, according to the present invention, the number of sub-sampling units installed around the main sampling unit may be variably adjusted.

As not shown, according to the present invention, the gap between the sub-sampling unit and the main sampling unit may be effectively adjusted.

The extension frame of the sub-sampling unit includes a multi-stage pipe.

The multi-stage pipe may be formed in a multi-stage extension type so that the length of the multi-stage pipe may be adjustable and the multi-stage pipe may be fixed at a predetermined position with a bolt.

Therefore, according to the sampling positions of the present invention, the main sampling unit and the sub-sampling unit may be adjusted according to the purpose of research.

In addition, as not shown, according to the present invention, a supplementary weight storage unit for storing a predetermined weight may be detachably installed the sub-sampling unit.

The supplementary weight storage unit may include a rotational door closing or opening the supplementary weight storage unit in cooperation with the elevating operation of the trigger.

The supplementary weight storage unit may be selectively provided to each sub-sampling unit.

That is, the supplementary weight storage unit may be detachably coupled to the sub-sampling unit. The detachable coupling scheme may include a coupling scheme of using a bolt and a nut.

Thus, according to the present invention, when the sub-sampling unit is detached from the main sampling unit, the sub-sampling unit may be received into a condition under which the sub-sampling unit independently collects samples from sea floor.

According to the embodiment of the present invention, samples such as a manganese nodule may be simultaneously collected from the same area of sea floor by using both FFG (Free-Fall Grab) and BC (Box Corer).

According to the embodiment of the present invention, both FFG and BC may be used simultaneously or independently from each other in order to collect samples from sea floor.

According to the embodiment of the present invention, the disadvantages of the FFG and BC may be supplemented with each other in the aspect of the sampling result from sea floor.

According to the embodiment of the present invention, samples may be exactly collected without any error of a sampling position due to an oceanic current variation and a current meteorological state.

According to the embodiment of the present invention, the FFG and BC may be complexly used so that the time taken to collect samples may be reduced.

According to the embodiment of the present invention, the samples collected by the FFG and BC may be compared with each other, so that the sampling efficiency of the FFG may be measured.

According to the embodiment of the present invention, two FFGs may be installed to both sides of the BC and the amounts of sampled collected by each FFG may be measured, so that the error range may be reduced.

INDUSTRIAL APPLICABILITY

The present invention may collect samples such as a manganese nodule from the same area of sea floor by simultaneously using both FFG and BC.

Further, the present invention may use both FFG and BC simultaneously or independently from each other in order to collect samples from sea floor.

In addition, the present invention may supplement disadvantages of the FFG and BC with each other in the aspect of the sampling result from sea floor.

The invention claimed is:

1. A complex sampling apparatus, comprising:
   a main sampling unit having a predetermined weight to be sunk to sea floor and inserted into the sea floor in order to collect a sediment-including sample;
   one or a plurality of sub-sampling units disposed at a side of the main sampling unit; and
   an image acquiring unit installed to the main sampling unit to acquire an image of the sea floor,
   wherein the one or a plurality of sub-sampling units includes:
      an extension frame extending from a side of the main sampling unit;
      a trigger disposed on the extension frame, the trigger configured to receive an external force through contact with the sea floor to detect that the sub-sampling unit arrives on the sea floor; and
      a pair of grabs formed in a plate shape having a first end hinged to the extension frame, and wherein second ends of the pair of grabs are connected to each other through a mesh net configured to scrape a predetermined amount of a sample from a surface of the sea floor.

2. The apparatus of claim 1, wherein the main sampling unit includes:
   a weight connected to a wire wound by an external force;
   a sample box installed to a bottom end of the weight and having an opened bottom end to temporarily store the sediment-including sample;
   a spreader hinged to the weight and having one end connected to the wire and an opposite end tightly sealing an opening of the sample box; and
   a support frame to support the weight, the support frame having a lower end landed on the sea floor.

3. The apparatus of claim 2, wherein the sub-sampling unit disposed at the side of the main sampling unit further includes:
   an elastic member to provide an elastic force in a direction allowing the pair of grabs to be closed to each other; and
   a fixing member hinged to the extension frame to fix the grabs to allow the grabs to be away from each other,
   wherein the trigger is disposed in an upright state elevated on the extension frame and extending from a side of the support frame, and
   wherein the trigger releases a fixed state of the fixing member by using the wire when a bottom end of the trigger receives the external force through contact with the sea floor.

4. The apparatus of claim 3, wherein the fixing member includes a fixing protrusion inserted into a fixing groove formed on a circumference of one of the grabs, the trigger includes a roller rotated on a top end of the trigger, and the roller is connected to the fixing protrusion through a wire.

5. The apparatus of claim 3, wherein the sub-sampling unit includes a supplementary weight storage unit which is detachably coupled to the sub-sampling unit and stores a predetermined amount of a heavy material, and the supplementary weight storage unit includes a rotational door to open or close the supplementary weight storage unit in cooperation with the elevation operation of the trigger.

6. The apparatus of claim 3, wherein the extension frame is detachably coupled to the support frame.

7. The apparatus of claim 6, wherein the extension frame includes a multi-stage pipe, a length of which is adjustable in a side direction.

8. The apparatus of claim 2, wherein the weight includes a plurality of unit weights different from each other, and its weight is adjusted by adjusting a number of the unit weights.

* * * * *